(12) United States Patent
Beecroft et al.

(10) Patent No.: US 7,236,243 B2
(45) Date of Patent: Jun. 26, 2007

(54) HAND-HELD SPECTROMETER

(76) Inventors: Michael Thomas Beecroft, 31595 Cala Carrasco, Temecula, CA (US) 92592; Marian Martin Szczesniak, 31615 Via Cordoba, Temecula, CA (US) 92592; Barry James Smith, 1355 Woodview Ct., Oceanside, CA (US) 92056; John Fujima Matsumoto, 216 Camino De Los Flores, Encinitas, CA (US) 92024; James Paul Ferguson, 29624 Iura Ct., Menifee, CA (US) 92884

( * ) Notice: Subject to any disclaimer, the term of this patent is extended or adjusted under 35 U.S.C. 154(b) by 0 days.

(21) Appl. No.: 11/103,699

(22) Filed: Apr. 11, 2005

(65) Prior Publication Data

US 2005/0229698 A1 Oct. 20, 2005

Related U.S. Application Data

(60) Provisional application No. 60/561,410, filed on Apr. 12, 2004.

(51) Int. Cl.
*G01J 3/18* (2006.01)
(52) U.S. Cl. ..................................... 356/328
(58) Field of Classification Search ............... None
See application file for complete search history.

(56) References Cited

U.S. PATENT DOCUMENTS 4,550,381 A * 10/1985 Waechter et al. ........... 250/369

* cited by examiner

*Primary Examiner*—Tu T. Nguyen
(74) *Attorney, Agent, or Firm*—John R. Ross; John R. Ross, III

(57) ABSTRACT

A hand-held portable modular spectrometer unit. The unit includes a detachable head containing a light source and optical components for detecting spectral information from light reflected from or transmitted through a target and a processor for converting the detected spectral information into digital information. The unit also includes a plug-in rechargeable power supply and a control module for controlling the components in the measurement head. The controller includes a computer processor for analyzing the digital information produced by the measurement head and a display monitor for displaying spectral information produced by the control unit. In preferred embodiments several measuring heads are available. Each of these measurement heads includes a spectrometer.

41 Claims, 16 Drawing Sheets

| Butane | | |
|---|---|---|
| Magnitude [mV] | Concentration [ppm] | Absorbance [a.u.] |
| 1071 | 0 | 0 |
| 1063.8 | 5 | 0.0029 |
| 1056.2 | 10 | 0.0061 |
| 945 | 100 | 0.0543 |
| noise | | |
| 1 | | 0.0004 |

FIG. 11A

| Ethylene oxide | | |
|---|---|---|
| Magnitude [mV] | Concentration [ppm] | Absorbance [a.u.] |
| 1000 | 0 | 0 |
| 997 | 10 | 0.0013 |
| 972 | 100 | 0.0123 |

FIG. 12A

HAND-HELD SPECTROMETER

The present invention relates to spectrometers and in particular to portable spectrometers. This application claims the benefit of U.S. Provisional Application Ser. No. 60/561,410 filed Apr. 12, 2004.

This invention was in the course of a SBIR Contract No. N41756-02-M-1045 with the United States Navy and the United States government has rights in the invention.

BACKGROUND OF THE INVENTION

Applicants' employer, Surface Optics Corporation, developed during the 1990's a series of small rugged portable spectrometers. Some of these units have been successfully marketed as model SOC400. These units were powered by a 12 volt power supply, such as a car battery and required the addition of an associated computer, such as a desk-top or lap-top computer, to operate. The units included optical components for producing illumination at a variety of controlled spectra. These components include systems utilizing broad band light sources and optical filters to produce illumination at several specific wavelengths. Interferometers were used to produce illumination at a series of wavelengths. These devices are very useful for measuring diffuse reflectance of a target or sample. The spectra of the reflectance can identify target material. These units have been engineered into modular systems in which various "heads" could be interchanged allowing a single unit to be used for a variety of purposes. These heads included (1) an attenuated total reflectance (ATR) head, (2) a specular 50 degree reflectance head, (3) a grazing angle 75 degree specular reflectance head, (4) a gas cell head, (5) an integrating sphere head. With some of the devices only a single spectral point is measured and in other devices several spectra data is measured. Features of these prior art devices are described in the following patents, all of which are incorporated herein by reference:

U.S. Pat. Nos. 5,424,543, 5,821,535 and 5,949,074 describing imaging spectrometer units and U.S. Pat. Nos. 5,714,758 and 6,147,350 describing rugged portable units with Fourier transform infrared spectrometer illumination for diffuse reflectance spectral measurement.

The SOC400 has been a very successful product; however, the unit requires a separate power source and a computer as support equipment and in many applications a rolling cart to transport it. These components are depicted in FIG. 1 in the U.S. Pat. No. 5,714,758 patent. The measuring apparatus is depicted at 22 and the support equipment is depicted at 24. The support equipment includes a battery and a table-top computer 34 that controls the measuring apparatus, receives data there from, and stores the data, analyses the data, reports and/or displays the data.

What is needed in an even easier to use more compact modular portable spectrometer.

SUMMARY OF THE INVENTION

The present invention provides a hand-held portable modular spectrometer unit. The unit includes a detachable head containing a light source and optical components for detecting spectral information from light reflected from or transmitted through a target and a processor for converting the detected spectral information into digital information. The unit also includes a plug-in rechargeable power supply and a control module for controlling the components in the measurement head. The controller includes a computer processor for analyzing the digital information produced by the measurement head and a display monitor for displaying spectral information produced by the control unit. In preferred embodiments the plug-in rechargeable power supply is a 12-volt off-the-shelf power-tool rechargeable battery unit. In preferred embodiments several measuring heads are available. These include a gas cell measuring head, a surface reflectance measuring head that includes and integrating sphere, a specular reflectance measuring head, a grazing angle measuring head, an attenuated total reflectance measuring head, a diffuse reflection measuring head, a non-volatile residues measuring head, a liquid transmission cell measuring head and a fluorescence measuring head. Each of these measurement heads includes a spectrometer. Several types of spectrometers are available including those based on filters, prisms, gratings and interferometers. The unit can operate in a wide range of wavelengths including the infrared, visible and ultraviolet spectral ranges.

Important features of the invention include:

Utilization of cordless power drill basic shape for a scientific instrument.

Utilization of power tool off shelf battery as power source for a scientific instrument, in particular for a hand held spectroscopic monitor.

Modularity of the scientific hand held instrument allowing for interchangeability of measurement heads attached to a command module to accommodate variety of spectroscopic measurement techniques within the same tool. This concept:

lowers the manufacturing cost, lowers the cost to the user, presents a user with a suite of tools for field hand held analysis.

Ability of the measurement heads to function independently from the command module being replaced by a power and communication adapter.

A concept of a suite of scientific tools based on the same command module, with similar in look and operation replacement measurement heads for achieving variety of spectroscopic analysis in a portable hand held operation.

BRIEF DESCRIPTION OF THE DRAWINGS

FIGS. 11A and 11B are a butane gas calibration curve

FIGS. 12A and 12B are an ethylene gas calibration curve

DETAILED DESCRIPTION OF PREFERRED EMBODIMENTS

SOC410 Handheld Reflectometer

Figure 1:
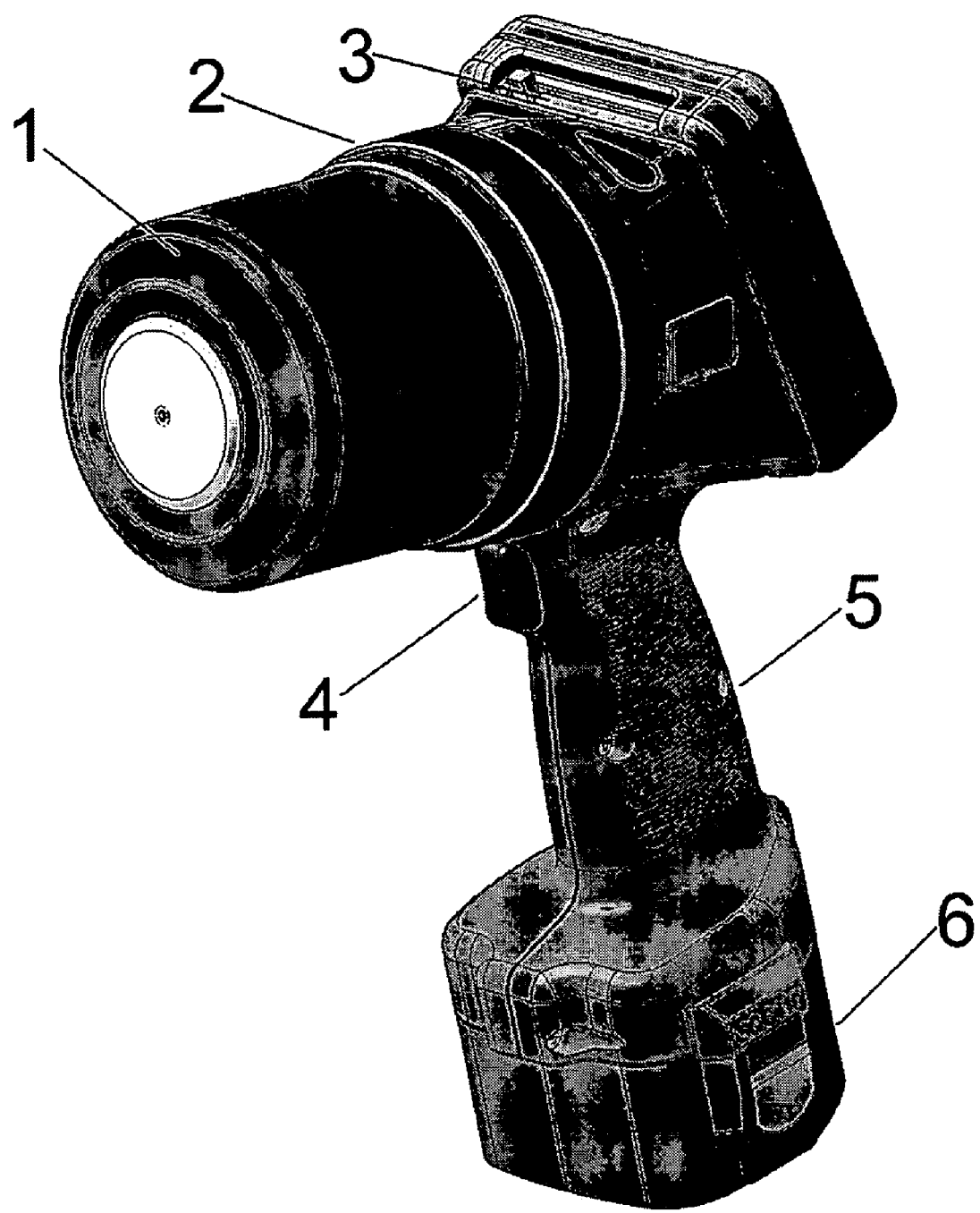
FIG. 1 is a front view of the SOC410 Handheld Reflectometer

FIG. 1 shows important features of a preferred embodiment of the present invention. It is now a standard product of Surface Optics Corporation. It is the SOC410 handheld reflectometer has several key features that are common to many handheld power tools. These include an easily replaceable rechargeable battery 6, an ergonomically designed handle 5, and a trigger 4 to start a measurement. The SOC410 is designed to have replaceable measurement heads 1 which are attached to the handle with a threaded collar 2. All the measured data is stored on a compact flash card 3 located at the top of the unit. The SOC410 is comprised of two modular pieces, the measurement head 1, 2 and the command module 3, 4, 5, 6. The measurement head contains all the necessary hardware to perform its intended function with the exception of a computer and power which is supplied by the command module.

Figure 2:
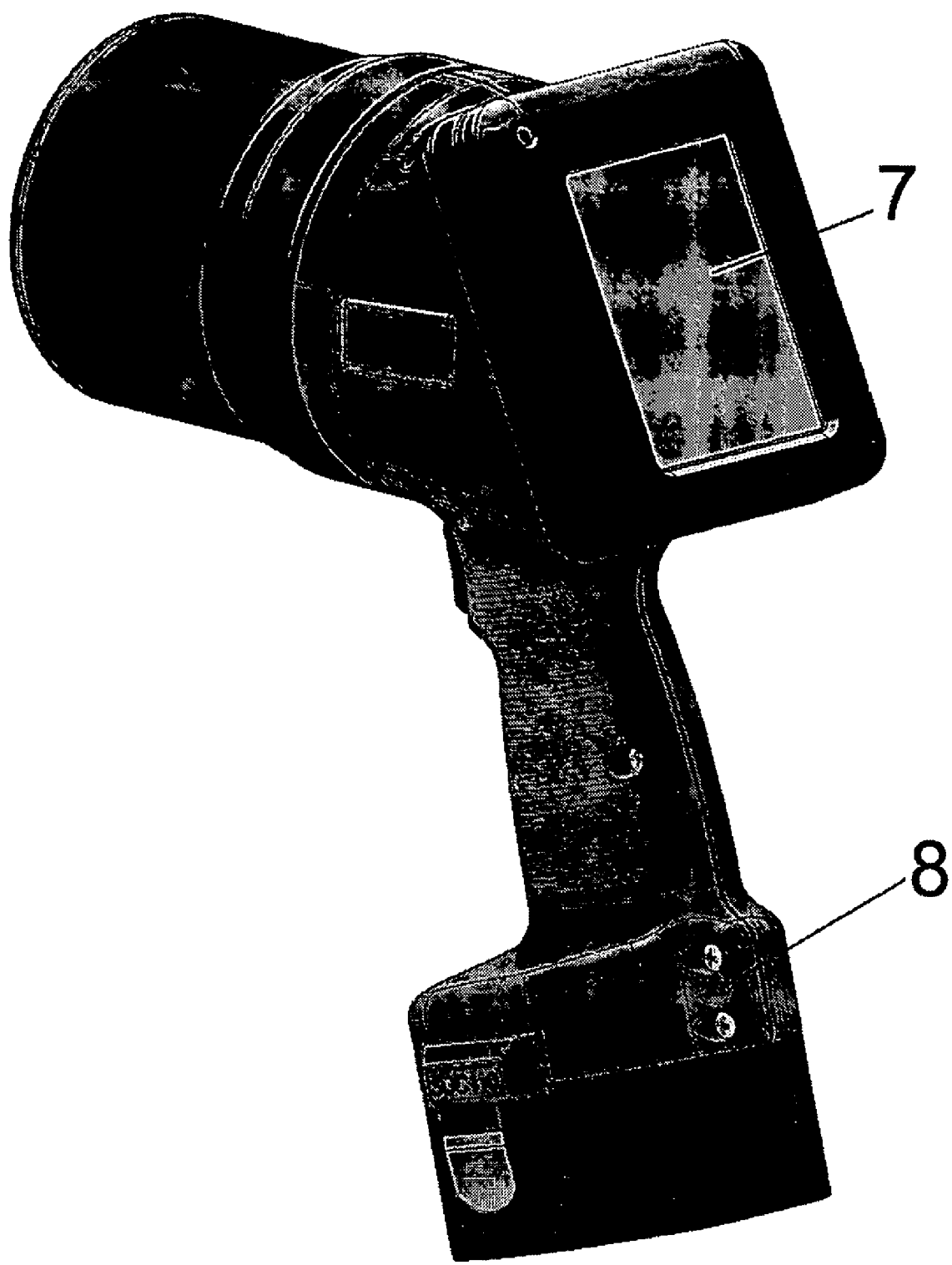
FIG. 2 is a rear view of the SOC410 Handheld Reflectometer

FIG. 2 shows a rear view of the SOC410 handheld reflectometer is operated using a QVGA (320 pixel×240 pixel LCD panel touch screen interface 7 and the trigger 6. The touch screen interface allows the user to select different modes of operation as dictated by the measurement head installed on the unit thru the use of software buttons displayed on the touch screen interface. When held in hand, a wrist lanyard device attaches to the handle 8 and secures the unit from accidental drops.

The SOC410 is designed to be held with a single hand. The measurement head is held up against the surface to be tested and the trigger is pulled to produce a measurement of the surface to be measured in the case of reflectometer heads. Depending on the type of head and spectral ranges measured, different surface analysis can be produced by each head. Other heads are designed to sample gases of liquids in which case they are not placed against a surface.

Command Module

The command module provides all the power and computer processing needed to operate a measurement head. It is designed to operate a variety of easily interchangeable measurement heads. It is packaged into a user friendly format which is very similar to the common battery operated power drill. This includes a pistol grip with trigger and a battery which inserts into the bottom of the handle. A computer is located in the handle and a touch screen display which faces the user during operation. The user controls the unit by selecting various software functions from the touch screen interface and pressing trigger when a measurement is to be made. Measurement heads are attached to the front of the command module using a threaded collar design which is rotated to secure the measurement head to the command module. Two electrical connections are made when attaching the measurement head. They provide power and data communications between the command module and measurement head.

It is important to note that the command module has the familiar shape of a cordless power drill and is easily carried in one hand leaving the other hand free to operate the computer via the touch screen interface. This cordless power drill form factor was intentional and its purpose is to provide a functional paradigm (how to use the instrument) that most people are familiar with and that is: insert battery for power, hold the unit using the ergonomic hand grip, and press the trigger when operating the unit.

Figure 3:
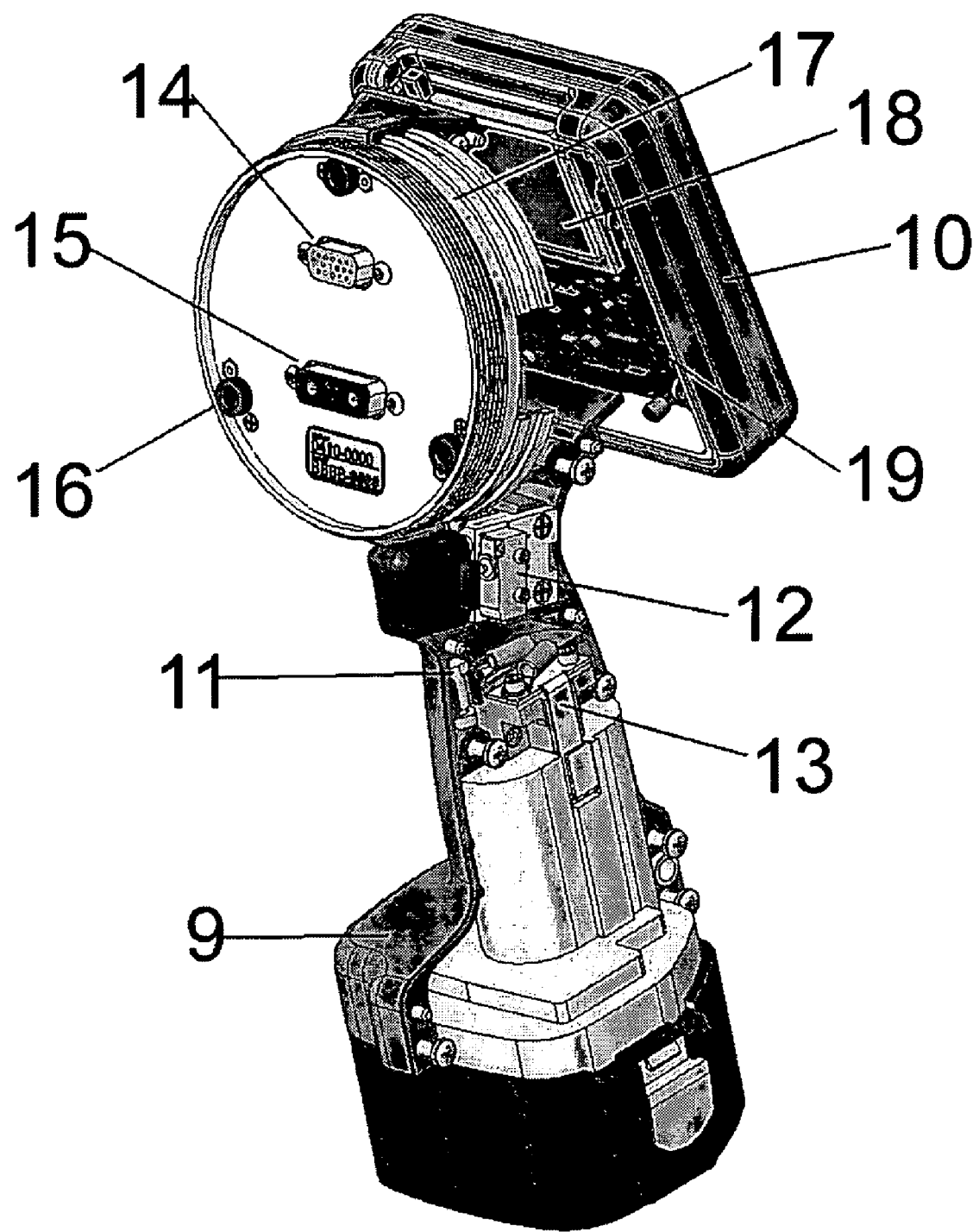
FIG. 3 is a front section view of the Command Module
Figure 4:
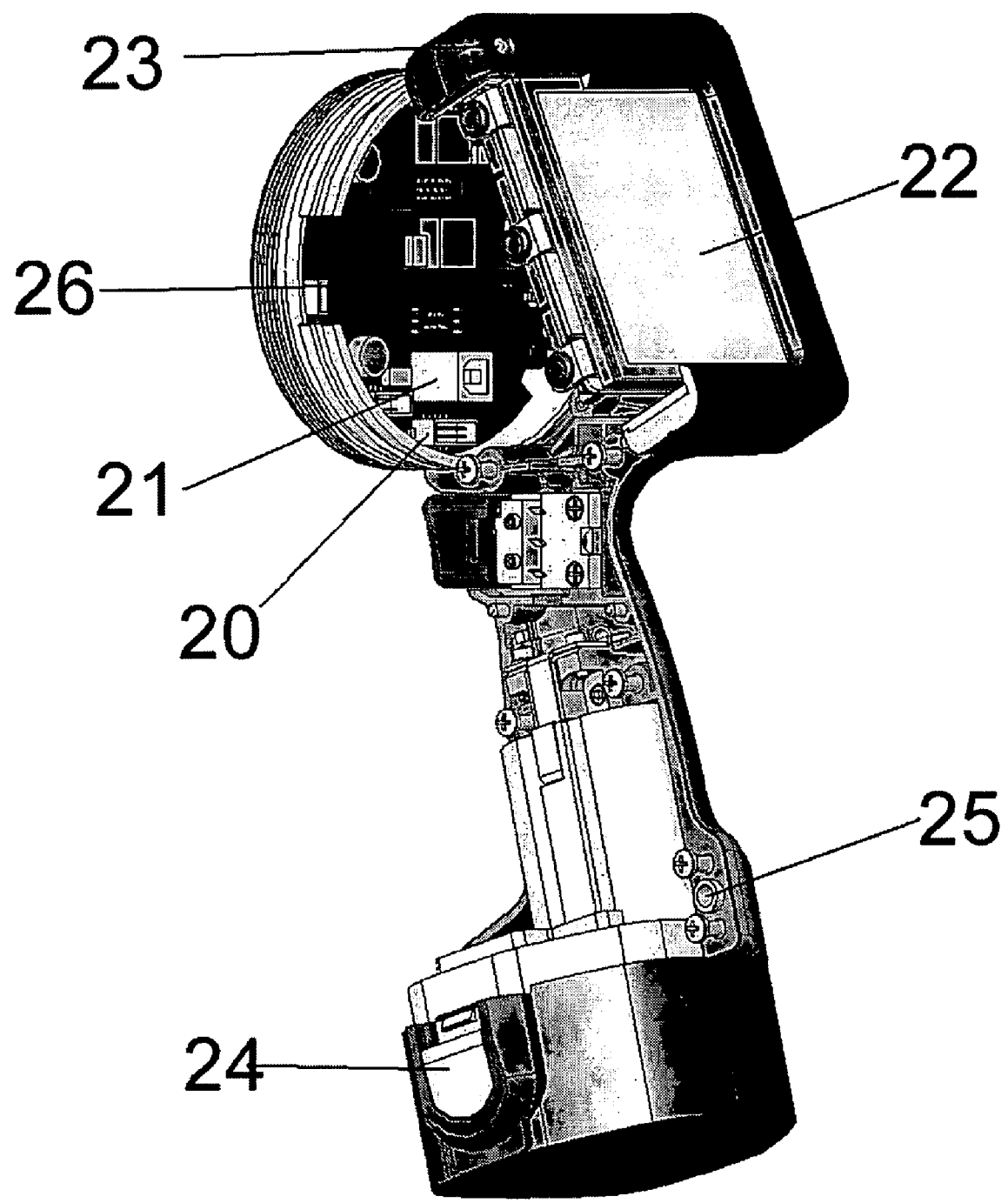
FIG. 4 is a rear section view of the Command Module

Referring to FIG. 3 and FIG. 4, details of the command module is shown. FIG. 3 is a front isometric section that reveals the internal workings. FIG. 4 similar to FIG. 3 except the view is from the rear of the command module and a portion of the computer & display assembly is shown in a section view. The primary structure is composed of two plastic shells 9 that are nearly mirror images of each other and, together, form a clam shell that holds all the internal sub-assemblies in place. Those sub-assemblies include computer 19 & display 22 which are located in a rubber armored housing 10, power supply 26 with interface connectors 14, 15 and integral threaded mating cylinder 17, trigger sub-assembly 12, and battery clip 13 sub-assembly. To support the various sub-assemblies, the plastic housing provides several other important functions which include a ergonomically design hand grip with a conveniently placed trigger 12 which can be used in the right or left hand. An interface for the battery complete with locking side tabs to lock the battery into place when inserting. A spring loaded catch 24 on the battery locks into these tabs located on either side of the handle. A thru hole 25 at the lower rear of the handle is used to attach a wrist strap to help secure the command module when in use (similar to a camera strap).

When the battery is completely inserted into the bottom of the handle, two nickel plated terminals in the battery clip assembly 13 make contact with the +/−terminals of the 12 V 2.6Ah Makita series #1234 battery. The 12-Volt DC power is routed up the Power Supply Printed Circuit Board (PCB) 26 via a wiring harness and plugs into the power input connector 20.

The Power Supply PCB 26 generates the several voltages needed to operate the measurement head and computer from the raw 12V supplied by the battery. Those generated voltages include +5VDC & −5VDC analog supply voltages for the measurement head and separate 5VDC & 3VDC digital supply voltages for the measurement head. A high density DB9 style connector 14 located on the front face of the command module is used to provide these voltages to the measurement head when it is attached. This connector also supplies the raw 12V battery voltage to the measurement head for future use if and when needed. This raw 12V voltage will protect the command module interface from obsolescence since future measurement heads will be able to generate their own voltages that were not originally planned for and thus are not provided here.

The Power Supply PCB 19 is mounted into a brass threaded ring 17 which the measurement head screws onto. On the front face of the command module are three alignment holes 16 that are used to guide the measurement head into place interchanging measurement heads. These alignment holes accept three alignment pins on the measurement head and prevent the electrical connector pins from being bent by improper alignment of the mating connectors when attaching a new measurement head.

In addition to the power supplied to the measurement head thru the power connector 14, the Power Supply PCB also provides several other functions. It provides three computer serial communication protocols which are USB 2.0, I2C, and RS232. The computer uses the RS232 to communicate with the measurement head by sending commands to control the measurement head and receiving data collected by the measurement head for processing. The USB 2.0 serial interface is provided thru connector 21 on the inside of the Power Supply PCB and is used by other embodiments of this invention to provide direct computer control using a standard desktop or laptop computer to operate the measurement heads without the need or the command module. The USB 2.0 is also available to talk with the embedded computer in future embodiments of this invention. A I2C communication link is used to talk with individual integrated circuits on all the PCB's. All communications between the command module and the measurement head are made thru the D-Sub Mixed Layout connector 15 when a measurement head is attached. The trigger is attached to this board which allows the computer to sense when the trigger is pulled. The trigger sub-assembly 12 is comprised of a trigger which slides on two spring loaded rails. When the trigger is depressed it closes a momentary style switch which is wired into the Power Supply PCB.

The Power Supply PCB 26 also supplies 7.5V power the computer and RS232 thru two connectors mounted on the rear of the PCB. The power and communications are wired into an industrial PDA (personal data assistant) style embedded computer 19 (Inhand Electronics model number Fingertip3). The computer runs Windows CE.net 4.1 operating system. A video display adaptor PCB is used by the computer to operate the Liquid Crystal Display (LCD) 22 (Sharp Electronics #LQ35Q7 DB02). This LCD comprises a QVGA screen which means that is has a resolution of 320×240 pixels or a quarter of a standard VGA screen. The screen is has a backlight which can be turned on or off to improve contrast and/or save battery life. It also has an integral touch screen interface which can be operated using a touch screen stylus or by applying pressure with a finger. This entire computer sub-assembly is protected with a rubber bumper guard 10 that surrounds the perimeter of the sub-assembly.

The user operates the unit by pressing soft buttons (buttons in the software) that are displayed on the LCD for the user. The LCD display also displays all the relevant data when a measurement is made. This data and the software are stored on a Compact Flash (CF) card 18 which is inserted into the top of the unit. This card can be removed and inserted in a laptop or desktop computer when data needs to be transferred to a PC. A Secure Digital (SD) card slot on the computer is also provided for future growth when needed. The use of the CF card allows vast amounts of data to be stored for later retrievable. CF cards are now commercially available that can hold as much as 1 gigabyte of data.

The user software provides the user interface for operating the SOC410. This software contains a variety of menus and buttons that allow the user to navigate thru the software to setup measurements, to run extensive diagnostics to test the integrity of the measurements, and to process the raw data once it has been measured.

During a measurement sequence the user is provided feedback by one of three different mechanisms, the touch panel display 22, a super bright LED 23, and a vibration motor 11 in the handle which is designed to vibrate the handle. Often during a measurement it is difficult to view the screen during the measurement sequence which may last several seconds during which time the user must hold the unit still. These three methods of feedback guarantee that the user will get the required feedback indicating the completion of measurement regardless of the user/SOC410 orientation.

Attenuated Total Reflectance Measurement Head

Figure 5:
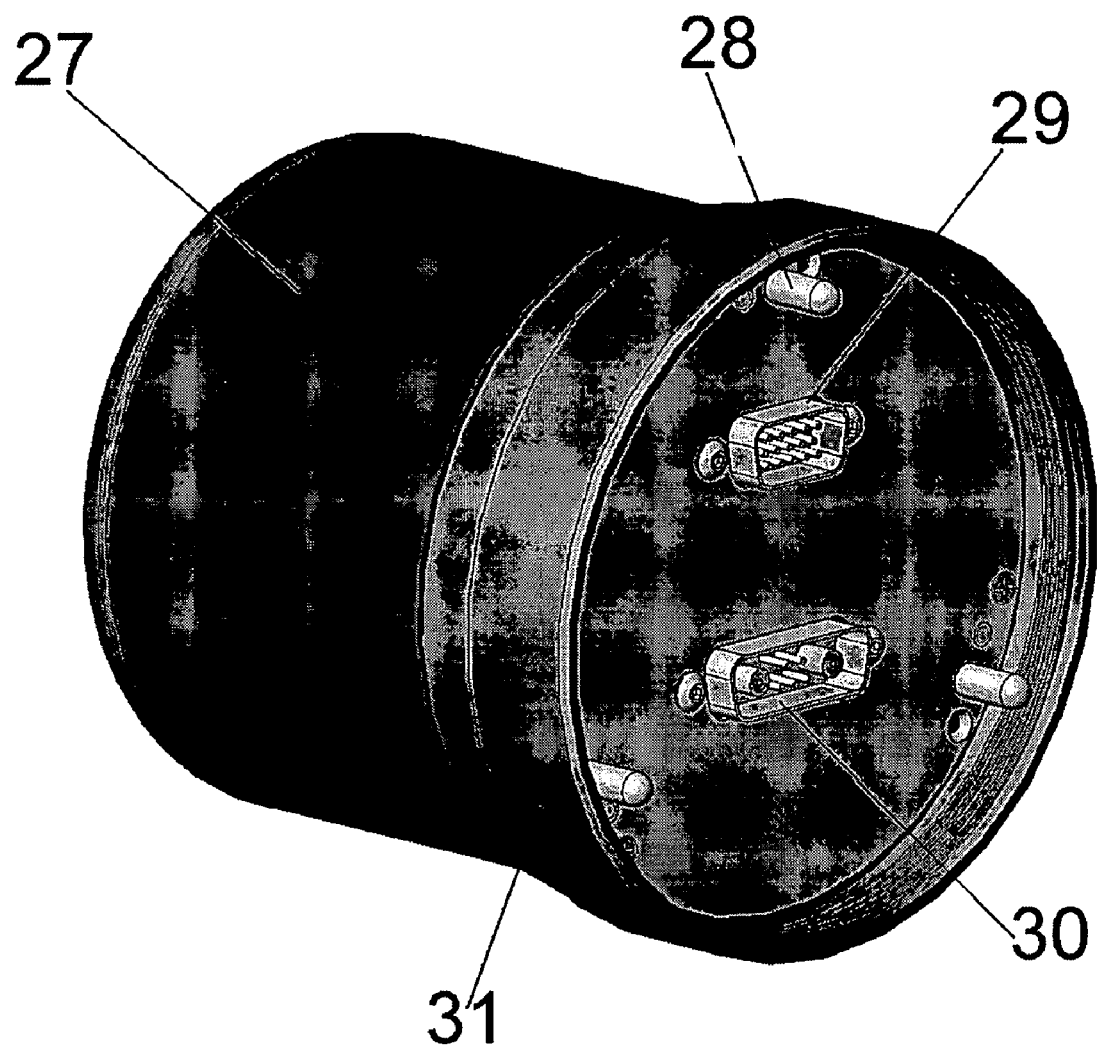
FIG. 5 is a rear view ATR measurement Head

A first preferred measurement head is the Attenuated Total Reflectance (ATR) measurement head. Referring to FIG. 5, a rear view of the ATR measurement head is shown. This rear view is typical of all the measurement heads in that it has several features that all measurement heads have in common. A thread collar 31 is used to secure the measurement to the command module. Three alignment pins 28 accurately align the measurement when attaching to the command module such that both interface connectors 29, 30 are properly orientated. An aluminum cover 27 protects all the internal mechanisms for the environment.

Figure 6:
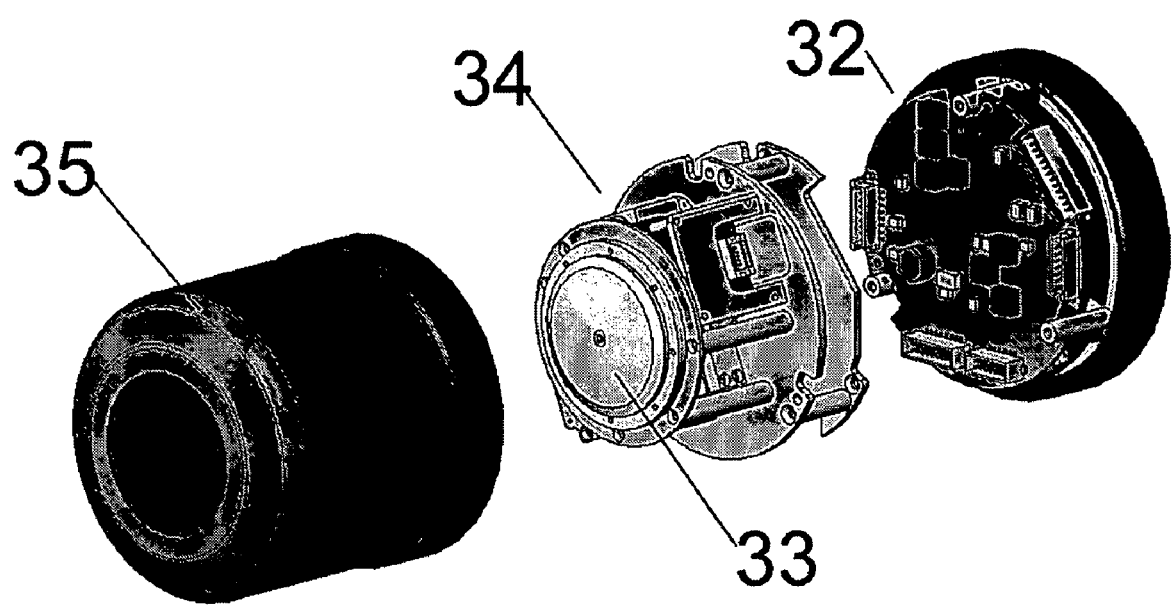
FIG. 6 is an exploded view ATR measurement head

FIG. 6 is an exploded view of the ATR measurement head showing the three major assemblies that comprise the head. These are the electronics module 32, the optical assembly 34, and the aluminum cover 35. The front face of the measure head 33 is pressed against the sample during a measurement. Again, as stated earlier, all the measurement heads share these three assemblies in different forms. In fact, the electronics module 32 is common to all the different embodiments of the measurement heads describe herein.

Two separate electronic printed circuit boards (PCB's) located in the electronics module 32 provide much of the electrical related functionality for the measurement head. One PCB is a digital communication board which handles three communication protocols: RS232, USB 2.0, and I2C. This board comprises a microprocessor that provides intelligence for the head. It controls an analog to digital converter, detector gain levels, chopper motors, a bandpass filter wheel, pivoting mirrors, source power, detector power and cooling, detector temperature monitor, measurement head temperature monitor, and monitors power supply voltage levels. This is achieved using direct digit IO lines and the I2C interface. This board also comprises mating portions of power supply connector 29 and digital communications connector 30 that mate to the power supply board inside the command module.

The second major PCB is analog board that provides DC motor circuitry for up to three motors. In this embodiment the motors are used to control an optical chopper shown in FIG. 7 at 37 and 34 and bandpass filter wheel 39. This board also provides circuitry for biasing the detector and thermoelectrically cooling the detector. Many detectors do not require biasing or thermoelectric cooling in which case this circuitry would sit idle. Also in other heads different motors are utilized but the same electronics module can be used interchangeably.

Optical Assembly

The optical assembly is the assembly that defines the type of data each measurement head is used to collect. It is where are the work is done. Whereas each measurement head has the same electronics module and functionally equivalent covers, the optical assembly is always different in both form and function. The optical systems can all be reduced to 5 components and they are:

1) the source 43,
2) optical chopper 37,
3) the sampling optics which in this case is the ATR crystal 36,
4) the spectrometer which in this case is bandpass filter 39, and
5) a detector 40.

Figure 7:
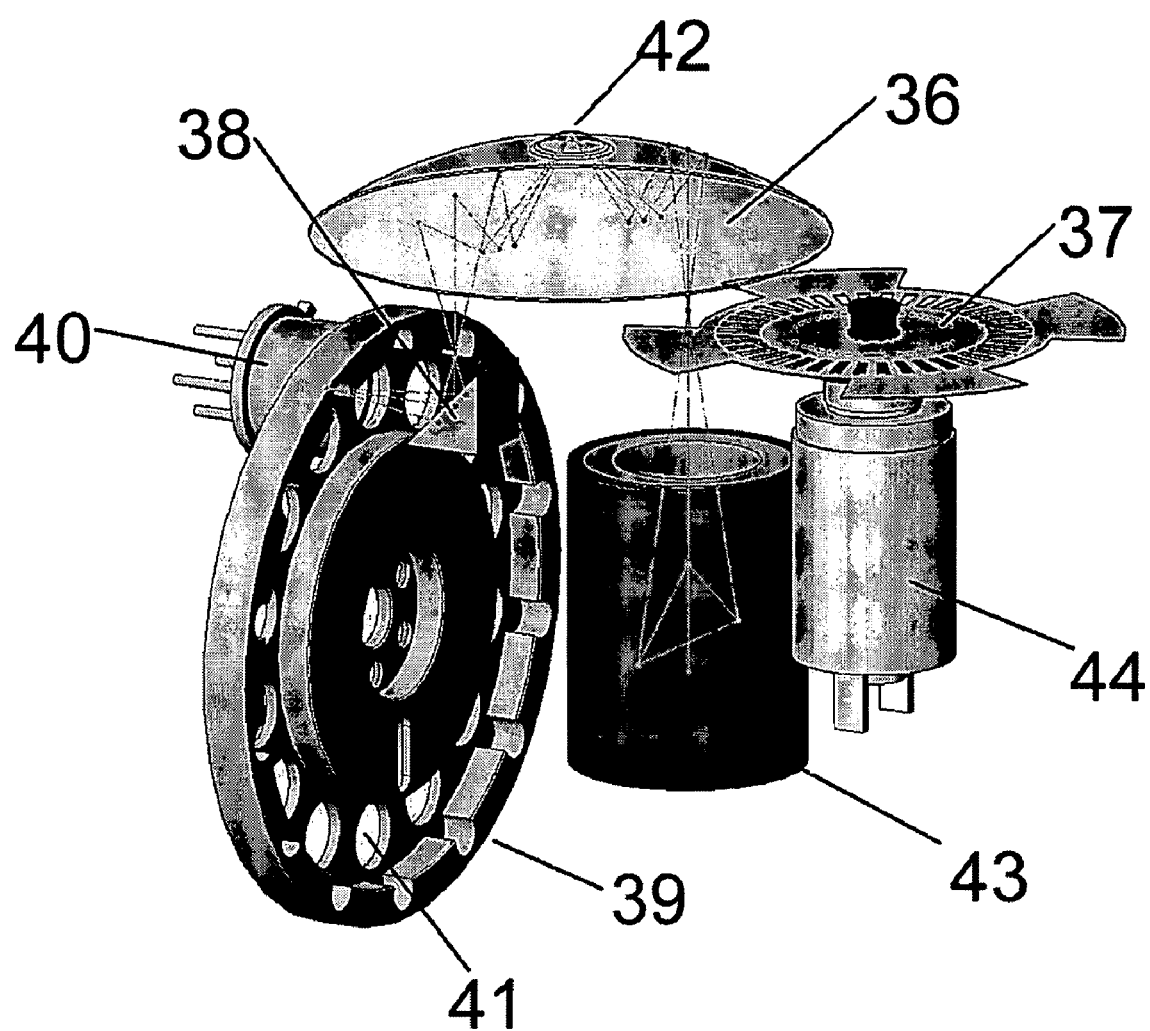
FIG. 7 is an ATR measurement head optical layout

FIG. 7 shows the optical assembly with just the important optical components exposed. The optical train for the ATR measurement head begins at the source 43. The source in the ATR embodiment is an electrically heated incandescent Kanthal filament source sealed in an inert argon environment behind an IR transmissive window of ZnSe. This source is manufactured to specification by Carley Lamps. The source power is computer controlled via the electronics module 32 and can be varied from 0 to 6 volts depending on the requirements of the measurement head and measurement to be performed.

The source is focused thru a miniature optical chopper 37 that modulates the light for better signal to noise performance. The voltage to the chopper motor 44 is also controlled via the electronics module 32 and can be varied to change the speed of the motor. This changes the frequency that the light is modulated. The modulated light bounces thru the Diamond ATR crystal 36 supplied by Pike Technologies (U.S. Pat. No. 5,965,889). The modulated light strikes a diamond face 42 in the crystal where it is totally internally reflected when exposed to air. When pressed against a sample some of the light is absorbed to varying degrees depending of the wavelength and the sample that the diamond face 42 is pressed against. In this embodiment the ATR crystal are the sampling optics which are used to probe the physical nature of the sample.

After bouncing thru the ATR crystal 36 (requiring at least five discrete bounces), the light is directed thru the spectrometer, a bandpass filter wheel 39 via a fold mirror 38. The computer controlled bandpass filter wheel 39 can be rotated into one of fourteen different positions 41. At different positions a different bandpass filter would be mounted which would measure a different spectral band. After the light passes thru a particular bandpass filter in the bandpass filter wheel it is measured by the detector. In this case a DTGS pyroelectric detector is used and it is provided by British Aerospace Engineering part number P5121. Each measurement head embodiment is capable of using different detectors depending of the requirements of the measurement head. The detector senses the modulated light which is then converted into a digital signal and sent to the electronics module for processing. The electronics module demodulates the signal and passes that on to the computer in the command module for final processing over either the RS232 line or the USB 2.0 line.

The remaining measurement head embodiments describe here are all very similar to the ATR measurement head. They all have the same electronics module, a functionally equivalent cover, and an optical assembly. The optical assemblies of all the measurement heads all share five basic components, a source, an optical chopper, sampling optics (in this case an ATR crystal), a spectrometer (in this case bandpass filter wheel), and a detector (in this case a DTGS pyroelectric detector).

Specular 50 Degree Angle Reflectance Measurement Head

The specular 50 degree reflectance measurement head embodiment is nearly identical to the ATR measurement head embodiment. The only difference is the sampling optics which determines how the sample is probed. In this case the sample's specular reflectance is measured at an angle of 50 degrees. As such, only the optical assembly is discussed here since all other details are identical to the previous embodiment.

Figure 8:
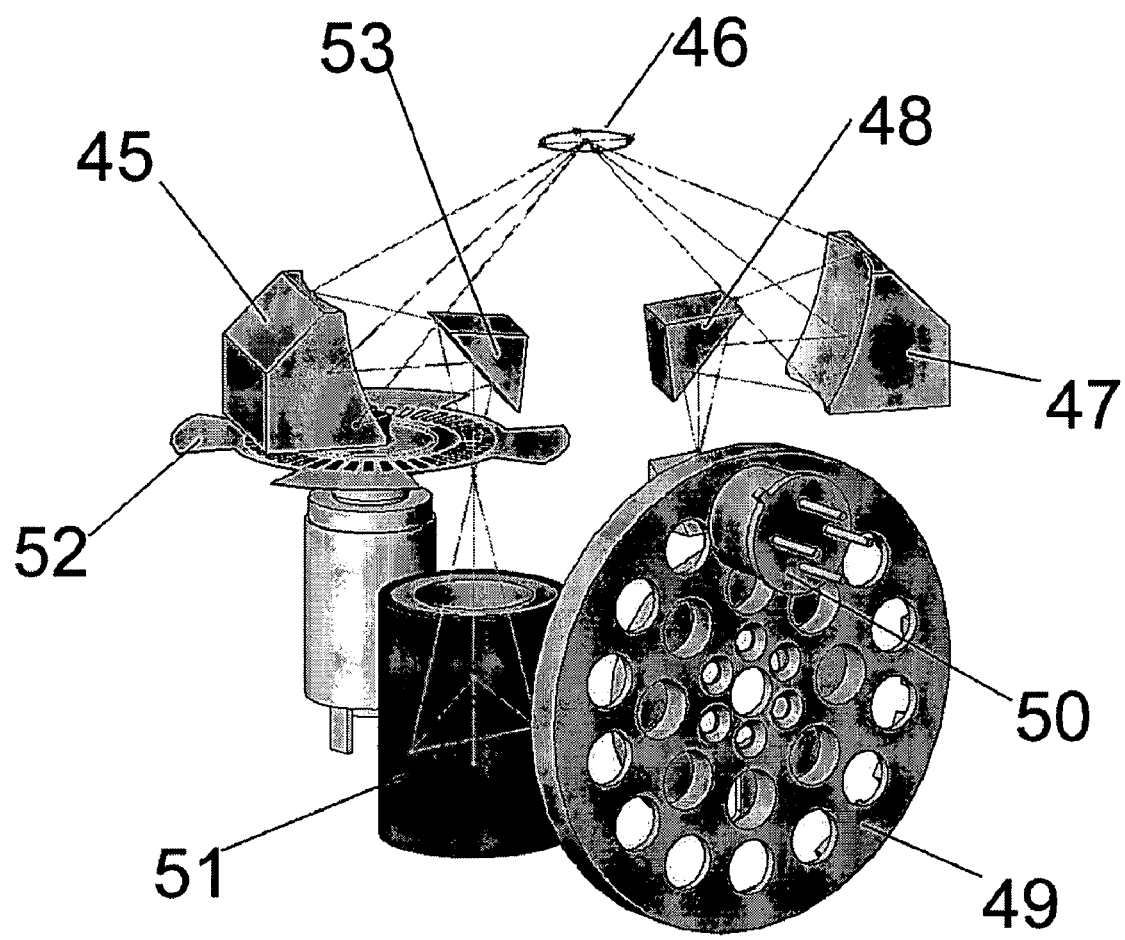
FIG. 8 is a specular 50 degree measurement head optical layout

Referring to FIG. 8, the optical layout of the specular 50 degree measurement head is shown. Again the optical layout starts with the source 51 which focuses the light thru an optical chopper 52 and into the sampling optics portion of the measurement head. Here the sampling optics are designed to illuminate the sample at 50 degree angle with respect to the normal of the sample. The light reflected into the 50 degree specular direction is then captured and directed into the spectrometer portion of the measurement head. This is accomplished with four different mirrors. The first fold mirror 53 redirects the modulated light from the source toward an elliptical mirror 45. This mirror focuses the beam onto the sample 46 which is represented schematically by an elliptical outline whose boundary illustrates the size of the beam on the sample. A faceplate at the front of the instrument precisely locates the sample at this focal point 46 when the measurement head is pressed up against the sample.

Typically, light is reflected off the sample in all directions. The elliptical mirror 47 only collects the light in the specular direction and funnels it thru a fold mirror 48 and into the spectrometer. In this case the spectrometer is the bandpass filter wheel 49. After the light passes thru the spectrometer, it is measured by a DTGS detector 50.

Although similar to the ATR measurement head, the specular 50 degree measurement head measures a different optical property entirely. Depending on the sample, one method or the other may be best for characterizing the surface to be measured.

Grazing Angle Reflectance Measurement Head

The grazing angle reflectance measurement head embodiment is nearly identical to both the ATR measurement head and the specular 50 degree angle reflectance measurement head embodiment. The only difference, again, is the sampling optics which determines how the sample is probed. In this case the sample's grazing angle reflectance is measured at an angle of 75 degrees. As such, only the optical assembly is discussed here since all other details are identical to the previous embodiments.

Figure 9:
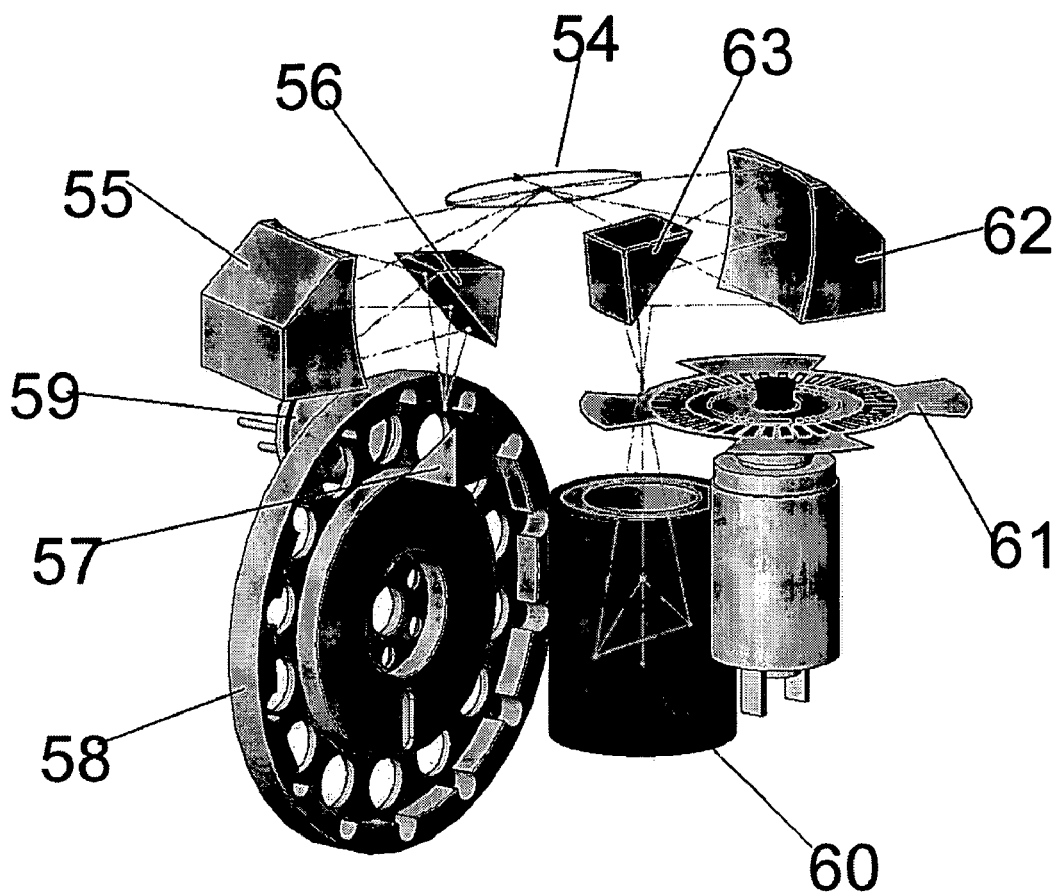
FIG. 9 is a grazing angle measurement head optical layout

Referring to FIG. 9, the optical layout of the grazing angle measurement head is shown from a different perspective than shown in the case of the specular 50 degree angle reflectance measurement head. Again the optical layout starts with the source 60 which focuses the light thru an optical chopper 61 and into the sampling optics portion of the measurement head. Here the sampling optics are designed to illuminate the sample at a grazing angle of incidence with respect to the normal of the sample. The light reflected into grazing specular direction is then captured and directed into the spectrometer portion of the measurement head. This is accomplished with four different mirrors. The first fold mirror 63 redirects the modulated light from the source toward an elliptical mirror 62. This mirror focuses the beam onto the sample 54 which is represented schematically by an elliptical outline whose boundary illustrates the size of the beam on the sample. In this case the beam is a very eccentric ellipse because of the high angle of incidence the source beam. A faceplate at the front of the instrument precisely locates the sample at this focal point 54 when the measurement head is pressed up against the sample.

Typically, light is reflected off the sample in all directions. The elliptically mirror 55 only collects the light in the specular direction and funnels it thru a fold mirror 56 and into the spectrometer. This case the spectrometer is our bandpass filter wheel 58. The light from the fold mirror 56 strikes another fold mirror which sends the light into the spectrometer. After the light passes thru the spectrometer, it is measured by a DTGS detector 59.

Although similar to the ATR measurement and the specular 50 degree measurement head, the grazing angle measurement head measures a different optical property than either of these other two. Depending on the sample, one method or the other may be best for characterizing the surface to be measured.

Gas Cell Measurement Head

Infrared spectroscopy has been used from its beginning for analysis of matter in gas phase. By analysis is meant understanding of spectroscopic properties of gases. Once those were understood for a specific gas, this knowledge has been used to identify that gas, to detect its presence, and to quantitatively predict that gas concentration. Technical methods have been developed for all of those analyses. The device and method described here is a novel device and a novel method for gas analysis. Its main characteristic is its portability and modularity, its shape and way in which it can be utilized. There are many portable gas phase analyzers, especially utilized for detection of specific gases. However, all of them are packaged in form of boxes. All sorts of box shaped gas analyzers are available on the market. Some of them are miniature, some larger, some are equipped with wands for gas "sniffing". But they all are box like shaped. What we are proposing is a device which is shaped like a household power tool and to be used as a tool. In addition, the proposed gas analyzer constituted by the Command module and the Gas Head can be quickly modified into another gas (from methane to ammonia) analyzer just by replacing the measurement head on the Command Module. Further the Gas Analyzer can be quickly modified into a surface or powder analyzer just by changing the analytical head on the Command Module. Other aspects of this innovation are described elsewhere in the patent document.

Figure 10:
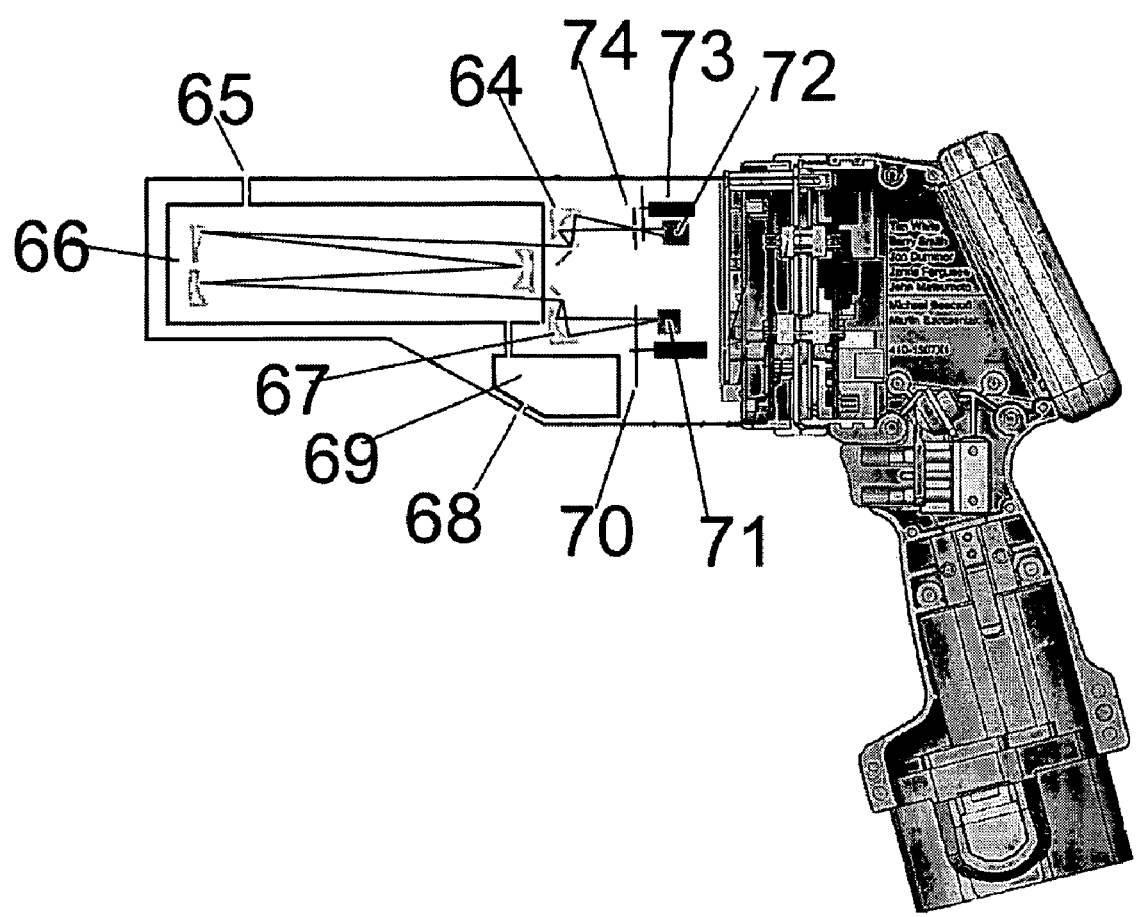
FIG. 10 is a cell measurement head

The gas cell embodiment of this invention is shown in FIG. 10. This is a modular hand-held gas cell spectrometer. It sucks gas from an environment into a cell and measures transmission of light through the sample at a variety of wavelengths to produce an absorption or transmission spectrum for the gas. The unit consists of a command module and a measurement head. Here is gas cell measurement head is shown attached to the command module which is illustrated in a section view and which was described in an earlier embodiment.

This measuring head is one of several measuring heads that can be utilized with this invention. This measuring head turns the present invention into a "gas sniffer" for monitoring gasses. Gas from an environment is sucked into gas cell 66 by gas pump 69 (miniature gas pump by Sensidyne) through gas inlet 68. The gas is exhausted through outlet 65. The head includes a light source 72 which in this preferred embodiment is a broad band infrared source custom built by Carley Lamps Inc. The emitting beam is focused at the aperture 74 after passing through a beam chopper 73. The spherical mirror 64 (Edmund Scientific Inc.) focuses the beam at the focal point of the White cell. A flat mirror directs the beam to the focal point of the gas cell. The beam travels thru the gas cell 66 in multiple passes. Each pass increases the optical path of the beam thru the gas cell which in turn increases the sensitivity of the device. The beam exiting the cell is refocused by a spherical mirror 67 thru a discrete narrow bandpass filter wheel 70 (the spectrometer) to the infrared light detector 71. In this embodiment a 10 cm base pass White gas cell 66 by Infrared Analysis Inc. is used. The total length of the optical pass is 2.5 m. Some of the beam intensity is lost due to multiple reflections and some of the energy is absorbed by the present gas. In preferred embodiments with the gas cell evacuated, about 90 percent of the beam passing through aperture 74 exits to filter wheel 70 and the portion passing the filters are detected in detector 71. The filter wheel comprises up to 8 filters each designed to pass only a narrow band of wavelengths. These filters are available from suppliers such as OCLI, or Barr Associates. The filter wheel is software controlled and each filter is spun into position and a measurement at the detector is made at the wavelength. Depending of the specific gas to be measured, several filters may be rotated into position to measure specific absorption bands to identify the gas and/or gas concentration. The filters are supplied by OCLI. The filter wheel is moved by a motor (MicroMo model number 1016M012GK380+10-1/16) controlled from the processor on the Digital Board. The output of detector 71 (by Cal Sensors BXT2S Series PbSe Detector) is initially amplified by the preamplifier board on which it is mounted. The signal is further processed by the Analog Board, and then by the Digital Board. From there the signal is sent over RS232 protocol and over the connector on the Digital board and the connector the Power Supply board to the PDA computer in the Command Module. In this impediment the gas Cell head is used to quantify presence of a know gas.

To perform a measurement the gas cell is filled with a spectrally neutral gas like nitrogen or dry air. The baseline signal is recorded $I_b$. Next, the cell is filled with gas mixture to be analyzed and a sample reading is recorded $I_s$. The ratio of the $I_s$ over $I_b$ indicates the quantitative amount of the analyzed gas. Surface Optics Corporation designed software operating on the PDA computer allows for instrument calibration and quantitative data predictions. A calibration curve is developed with gas mixtures of known analytical gas concentration present. That calibration curve is used for predictions of concentrations of analyzed gases.

Figure 11B:
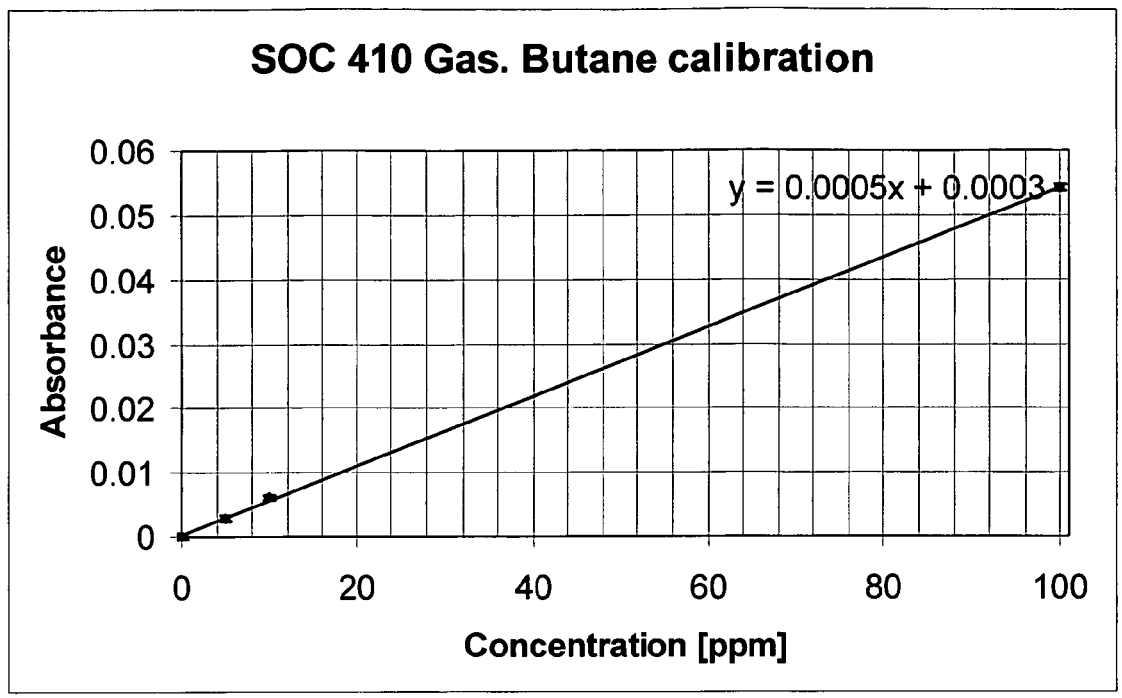
Figure 12B:
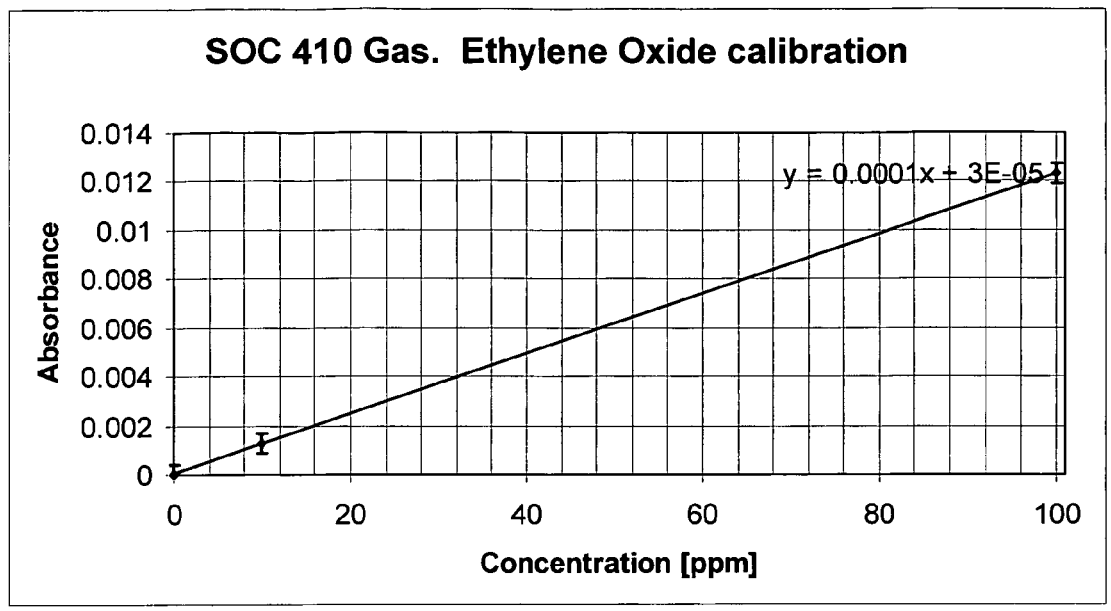

FIGS. 11A and B and 12A and B show the calibration curves for two different types of gases, butane and ethylene respectively. Was the calibration curve is established, the signal at the detector is linearly proportional to the gas being measured.

Directional Hemispherical Reflectance Measurement Head

Figure 13:
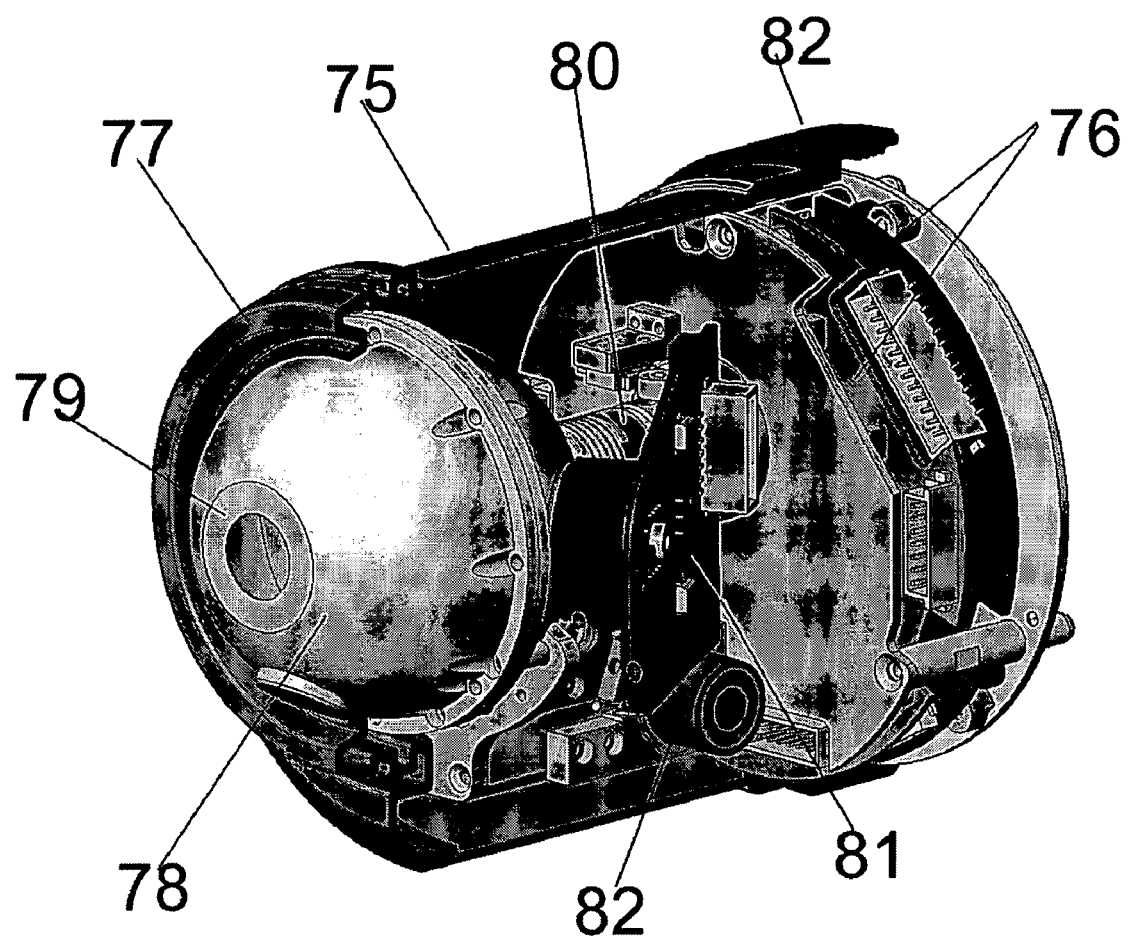
FIG. 13 is a directional Hemispherical Reflectance measurement head section view

FIG. 13 shows the Directional Hemispherical Reflectance (DHR) measurement head which contains all the optics and electronics needed to make DHR measurements. The only parts that are missing are a computer to display the results and a power supply to power the unit. This measurement head is designed to measure total hemispherical reflectance at two incident angles (20 degrees and 60 degrees) at six different wavelengths of interest. To accomplish this an integrating sphere with specialized source optics for illuminating the sample at two incident angles are used. In addition, 6 different detectors are also used to measure the six wavelengths of interest.

The DHR measurement head is comprised of three different assemblies and they are the electronics module 76, 82, the cover 75, 77, and the optical assembly 78, 81, 80. The electronics module is the same as that which was described earlier. In the case the cover has a front rubber boot 77 which is designed to flex during a measurement unlike previous covers mentioned in the previous embodiments. The optical assembly is what separates this measurement head from previous measurement heads. The integrating sphere 78 is mounted at the front of the unit and is designed to make contact with the sample at the sampling port 79 of the integrating sphere. The view in FIG. 13 also shows the preamp for the PbSe/PbS 4 band detector 81, and the IR source 82. The entire optical assembly is mounted on a flexible coupling 80 that suspends the optics in the middle of the unit. This coupling is designed to allow the entire optical train to move and conform to the sample surface when the sample port on the integrating sphere is pressed against the sample.

The flexible coupling is attached to an internal bulkhead inside the DHR measurement head. Behind this bulkhead sits two additional electronic boards that make up the electronics module 82.

Figure 14:
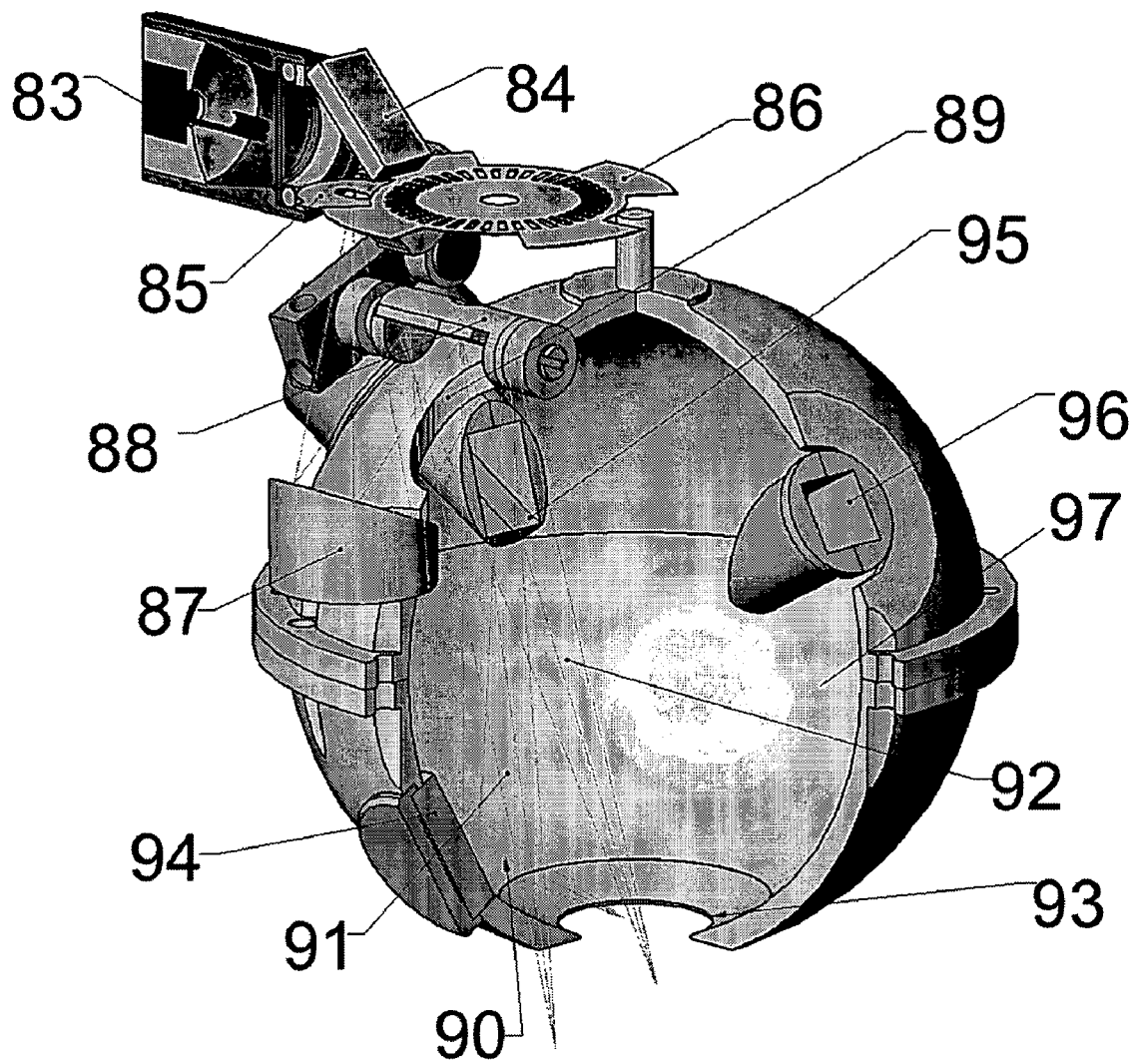
FIG. 14 is a directional Hemispherical Reflectance Integrating Sphere

FIG. 14 illustrates the complete optical path from source to sample to detector for the SOC410 DHR Head without the supporting mechanical structure or electronics. As with any optical reflectometer we must start at the source 83. A cut-away view of the source shows the filament mounted inside a cylinder. A rear elliptically shape reflector focuses the energy out thru a ZnSe window. At peak temperatures, the source filament (Kanthal filament) reaches temperatures of approximately 975 deg Celsius. The ZnSe window seals in the inert Argon environment that prolongs the life of the source filament. As a result, the filament is not exposed directly to the internal atmosphere of the unit. This is an important consideration when measuring materials in the presence of volatile gases.

A fold mirror 84 redirects the source beam thru a optical chopper 86 and onto an elliptical aperture 85. The optical chopper 86 is used to modulate the light to improve signal stability and signal to noise while the elliptical aperture 85 is designed to control the illuminated area on the sample.

The illuminated aperture is imaged onto the sample by an elliptical mirror 87. This mirror sits just below the aperture and redirects the incoming beam upward at a 45 degree angle onto the pivot mirror 88. The pivot mirror directs the beam into the integrating sphere thru the incident beam port 89 on the upper half of the sphere. The pivot mirror is named because it pivots about one of three positions. These positions are called the 20 degree incident beam 92, the reference beam 91, and the 60 degree incident beam 90. The 20 degree incident beam 92 position directly illuminates the sample port at approximately 20 degrees. The reference position strikes the side of the integrating sphere. The location of the integrating sphere that the reference beam strikes is specular so that the beam is reflected up into the upper hemisphere. The 60 degree incident beam 90 hits a 60 degree fold mirror 94 on the side of the integrating sphere which then redirects the light onto the sample port at an angle of approximately 60 degrees.

The integrating sphere sample port is pressed against the sample to make a measurement. The pivot mirror is rotated thru its various positions during a measurement at which point the sample is illuminated at 20 and 60 degree incident beam. The sample is typical removed when the reference beam is measured. All three beam positions result in light being scattered up into the integrating sphere.

The integrating sphere 97 interior surface is largely composed of a sandblasted gold plated aluminum surface. The exceptions being the ports, the 60 degree fold mirror (specular gold coating), and the spot on the integrating sphere that the reference beam hits (specular gold coating). In fact, all the optical mirrors in the system are gold coated with the exception of the source which is polished aluminum.

The light scattered into the integrating sphere bounces around until it is absorb by the gold coating, the sample, escapes out the incident beam port, or passes thru either of two detector baffles. The light traveling into the detector baffle and onto the detector is what is measured. This voltage measured at the detector is directly proportional to the reflectance of the sample when the sample is located at the sample port.

Two detector ports are used to allow 6 different detector elements to view the interior of the integrating sphere. The baffles prevent the detector from viewing the sample directly. Three PbSe detector elements and 1 PbS detector element is housed inside a single thermo-electrically cooled package and sees into the integrating sphere thru one baffle 95. Each detector element has a filter placed above it so that it only sees the band of interest which in this case are 3–5 um, 3–4 um, 4–5 um (all PbSe) and 1.5–2.5 um (PbS) bands. The second detector baffle 96 is used for a DTGS (8–12 um) and Silicon diode (0.7–1.1 um) detectors.

This entire optical measurement assembly is mounted on a flexible universal coupling 80. It is important to the integrity of the measurement that the sample port 79 is pressed squarely up against the sample surface. Without this flexible coupling the user would have to the entire unit very precisely perpendicular to the sample surface during a measurement. This is very difficult to due if not impossible in many situations. The flexible universal coupling allows the user to push the measurement head up against the surface and it will compliantly align itself without requiring the user to hold the unit very still during a measurement.

Other Measurement Heads

Diffuse Reflectance Measurement Head

Diffuse reflectance is a popular method for analysis of powder materials and surfaces with rough finish. Surface Optics Corporation developed a diffuse reflectance measurement head for the SOC 400 FTIR in 1995. The Diffuse Reflectance Measurement Head is not a typical infrared accessory. It is not an accessory at all. Surface Optics Corporation introduced in mid 90 ties reflectance accessories with built in light detector (reflectance and transmission accessories for the SOC 400 FTIR. In the present embodiment, the source of infrared energy, optics, spectrometer, detector and most of processing electronics are in the measurement head. In addition to illumination and detection optics, the head comes with all the elements found in the first embodiment. It consists the following elements: digital electronic board, analog electronic board, source of IR radiation, chopper, illumination optics, reflective beam collection optics, focusing optics, filter wheel, infrared detector, other supportive electronics and a cover.

V-Sphere Measurement Head

VSphere is Surface Optics Corporation's invention and a unique way for detection, identification and quantification of nonvolatile components in solvents. It is used in the aircraft, spacecraft, industrial hygiene semiconductor, and other industries. The users are organizations like NASA, Boeing, 3M, Intel, Maxtor.

Liquid Transmission Cell Measurement Head

A liquid transmission cell measurement head can also be used with the command module. It is not a typical infrared accessory. It is not an accessory at all. Surface Optics Corporation introduced in 1990's reflectance accessories with built in light detector which include reflectance and transmission accessories for the SOC 400 FTIR. In this embodiment the source of infrared energy, optics, spectrometer, detector and most of processing electronics are in the measurement head. In addition to illumination and detection optics, it comes with all the elements found in the first embodiment. It consists of the following elements: digital electronic board, analog electronic board, source of IR radiation, chopper, illumination optics, reflective beam collection optics, focusing optics, filter wheel, infrared detector, other supportive electronics, and cover.

Fluorescents Measurements

The fluorescents measurements measurement head may also be used with the command module. It is not a typical infrared accessory. It is not an accessory at all. Surface Optics Corporation introduced in mid 90 ties reflectance accessories with built in light detector which include reflectance and transmission accessories for the SOC 400 FTIR. In this embodiemnt the source of infrared energy, optics, spectrometer, detector and most of processing electronics consists of the Specular Reflectance measurements head. In addition to illumination and detection optics, it comes with all the elements found in the first embodiment. It consists of the following elements: digital electronic board, analog electronic board, source of IR radiation, chopper, illumination optics, reflective beam collection optics, focusing optics, filter wheel, infrared detector, other supportive electronics and cover.

Visible Color Measurements

A visible color measurement head can also be used with the command module. It also is not a typical infrared accessory. In this embodiment the source of infrared energy, optics, spectrometer, detector and most of processing electronics consists of the Specular Reflectance measurements head. In addition to illumination and detection optics, it comes with all the elements found in the first embodiment. It consist the following elements: digital electronic board, analog electronic board, source of IR radiation, chopper, illumination optics, reflective beam collection optics, focusing optics, filter wheel, infrared detector, other supportive electronics, and cover.

While the present invention has been described above in terms of specific embodiment, persons skilled in this art will recognize that many changes, additions and modifications can be made without departing from the novel concepts described above. Spectrometers are sophisticated devices but the components in them do not have to be. Applicants have made a better spectrometer by taking advantage of every-day off-the-shelf components. Two important ones are the personal digital assistants and power tool plug-in batteries.

Personnel Digital Assistants

Prior art spectrometers are typically equipped with specialized computer processors that are specially selected or designed for the spectrometer application. These processors typically require specialized software programming. An important feature of preferred embodiments of the present invention is the use of off-the-shelf personal digital assistants using Microsoft Windows CE. This computer has computer power and costs less than the more specialized embedded microcomputer systems used in the prior art spectrometers. Software development tools for commercial PDA's are quite sophisticated and help dramatically improve software productivity.

Power Tool Plug-In Battery

Applicants believe they are the first to incorporate power tool batteries into a hand held spectrometer. The result is a lower-cost, better performing, more easily handled spectrometer. Advantages of these batteries include high capacity (watt-hours) quick recharge and quick and easy battery interchange. They are small and compact. They provide a significant voltage level (12V) and high current draw. They use environmental friendlier technologies such as Ni-MH versus Ni-Cadmium (heavy metals) when it comes to the disposal of depleted batteries. They are also conveniently located at the bottom of the handle and thus provide a natural counterweight that balances the instrument in the hand of the user. The preferred battery is made by Makita and it is the same battery used for many hand held drills. It provides enough power to last for one to three hours. It lowers the spectrometer manufacturing cost. It lowers the maintenance cost. The replacement batteries are easily available form most of local hardware stores.

Interchangeable Measurement Heads

An important feature of the present invention is its interchangeable measurement heads. Prior art portable spectrometers had interchangeable measurement heads; however, these prior art devices required the user to remove a front cover, unhook the electrical connection, unbolt the accessory and then reverse these operations after placing the new head into the control unit. Measurement heads of the present invention can be interchanged with tow twists of the wrist. This is accomplished by integrating the mechanical and electrical connections such that both are made in one operation. A threaded collar on the outside of the measurement is rotated to make both mechanical and electrical connections with out the need for removing any covers or using any tools to remove covers or attach accessories.

Intelligent Measuring Heads

Measurement heads of the present invention are actually quite smart. Each is fully self-contained, just add power and connect USB cable to a computer and they are fully operational. In normal operation, command module 30 provides the power and the computer interface. However, each measurement head can operate with a laptop, tablet, or desktop computer via a USB computer interface and a small AC power supply or battery power supply. Each measurement head contains an embedded microprocessor which provides all the processing capability and the USB computer interface needed to run the measurement head. The source, optics, detector, ADC electronics, and microprocessor are contained within the head. Such an arrangement can be useful when extensive measurements are to be made in an industrial or laboratory environment when portability is not needed or when a higher computer power than is available in the control module is needed. The measurement heads of a hand held spectrometer function without command module. They can be controlled from an external PDA, PC, notebook, or a custom made computer. The heads are fully functioning spectrometers. To function, they need an external electrical power. They can operate with no external computing power providing information by flashing lights, sounding signals, sending out analog or digital signals. They can communicate with manufacturing networks. They can be placed on robotic arms for unattended unsupervised inspections.

Diagnostic Capabilities

Precisely because each measurement head is self contained with all the components needed to provide a fully functioning measurement system, preferred embodiments of the present invention are also capable of running a complete range of self diagnostics aimed at determining the current performance of the measurement head and comparing it to its factory settings. Power levels are checked as well as all the mechanical and optical settings to test for component failure and current component status including optical alignment status. The measurement head will even be able to tell the user when the unit is not working within specifications, how far out of spec and what is wrong. This will allow the supplier to provide much better customer support in the event the unit needs service. This level of diagnostics also provides an important quality assurance element to the measurements for the user. Questions such as:

Is the unit operating within specifications?
Is it aligned?
Is it calibrated?

can now be answered each time the unit is used.

Wavelength Calibration and Diagnostics

Each head preferably is factory calibrated before sale. Heads are preferably calibrated using a Fourier transform infrared (FTIR) spectrometer for the task of determining actual measured spectra of the system as a whole. Each measurement head should be tested and certified for operation at specific design wavelengths (measurement head dependent) by injecting light into the optical train of the measurement head with the FTIR spectrometer. The light from the spectrometer will start at the source location inside the measurement head. The light will then traverse the entire optical train until it reaches the detector where an interferogram will be measured. A fast Fourier transform of this interferogram will give very precise wavelength calibration data on each head before shipping. This data will be store in each head in its processors memory for retrieval when needed.

Spectral Separation of Light Components

The present invention can utilize a wide variety of spectroscopic techniques for providing specific spectral light components for examining whatever needs to be spectrally examined, be it gas, liquid, paste, powder, solid object, residue or material surface. These techniques include:

Optical Filters
  Discrete Bandpass Filters
  Linearly Variable Bandpass Filters
  Circularly Variable Bandpass Filters
Grating Based Spectrometers
Prism Based Spectrometers
Etalon Based Spectrometers
FTIR Spectrometers
Acousto-Optical Based Spectrometers In addition to the wide range spectroscopic methods available for use with the present invention, the invention is not limited to the IR spectrum but can be used in the ultra-violet, visible, and near infrared. In fact, future improvements maybe made to adapt the present invention to monitor X-ray spectra, or emitted energies induced by electron, X-ray, or UV or visible beam illumination. Also, as indicated above, the unit can be adapted for use for various types of reflectance measurements and for and transmission measurements through solids, gasses and liquids.

Flexible Suspension Optics

The measurement optics of hand held spectrometers in preferred embodiments is suspended on a flexible mount to minimize effect of hand shaking on the recorded data. It also confirms the measurement optic to the local shape of the analyzed sample. The current design uses a motor shaft coupling. This coupling is also known under name of machine spring. This coupling is also known as spring loaded universal joint. It is used on some exotic applications like the wheel suspension of the Mars Rover. In this case it is used to mount optical elements of a hand held device.

Power Tool Ergonomics

The SOC410 in packaged into a power tool like ergonomics which Appllicants believe is new to this class of instruments. It makes for ease of use and well balanced (physically) instrument with the battery at one end and the measurement head at the other.

What is claimed is:

1. A hand-held portable modular illuminating spectrometer system comprising:
   A) at least one detachable measurement head comprising:
      1) a light source and optical components including a spectrometer for detecting spectral information from light reflected from or transmitted through a target and
      2) a processor for converting the detected spectral information into digital information, and
   B) a control module configured as a hand-held module comprising:
      1) a plug-in rechargeable power supply and
      2) a control unit for controlling the components in the measurement head, said control unit comprising:
         a) a computer processor for analyzing the digital information produced by the measurement head and
         b) a display monitor for displaying spectral information produced by the control unit.

2. The system as in claim 1 wherein the plug-in rechargeable power supply is a 12-volt off-the-shelf power-tool rechargeable battery unit.

3. The system as in claim 1 wherein said control unit comprises computer and display components of off-the-shelf personal digital assistants.

4. The system as in claim 3 wherein said control unit is programmed with Microsoft Windows CE software.

5. The system as in claim 1 and further comprising a plurality of additional detachable measurement heads.

6. The system as in claim 5 and further comprising detachment means for removing said head and breaking electrical connections in a single operation and for replacing said head with another head and making electrical connections in a single operation.

7. The system as in claim 6 wherein said detachment means comprises a threaded collar.

8. The system as in claim 5 wherein each measurement head is configured to operate with a laptop, tablet, or desktop computer via a USB computer interface and a small AC power supply or battery power supply.

9. The system as in claim 5 wherein each measurement head contains an embedded microprocessor which provides all the processing capability and the USB computer interface needed to run the measurement head.

10. The system as claim 5 wherein each measurement head comprises a microprocessor.

11. The system as in claim 5 wherein said head is configured for use in situations when extensive measurements are to be made in an industrial or laboratory environment, when portability is not needed or when a higher computer power than is available in the control module is needed.

12. The system as in claim 11 wherein said head is controlled from an external PDA, PC, notebook, or a custom made computer.

13. The system as in claim 5 wherein each of said heads comprises a functioning spectrometer operable with no external computing power providing information that can be communicated with manufacturing networks.

14. The system as in claim 5 wherein each of said heads is configured so that it could be placed on a robotic arms for unattended unsupervised inspections.

15. The system as in claim 5 wherein each of said heads is configured to be capable of running a range of self diagnostics aimed at determining the current performance of the measurement head and comparing it to its factory settings.

16. The system as in claim 5 wherein each of said measurement head are configured to warn the user when the unit is not working within specifications.

17. The system as in claim 5 wherein each of said measurement heads is factory calibrated before sale.

18. The system as in claim 5 wherein each of said measurement heads preferably calibrated using a Fourier transform infrared (FTIR) spectrometer for the task of determining actual measured spectra of the system as a whole.

19. The system as in claim 5 wherein each of said measurement heads tested and certified for operation at specific design wavelengths by injecting light into the optical train of the measurement head with a FTIR spectrometer, with light from the spectrometer starting at the light source location inside the measurement head and traversing optics within the head until it reaches the detector where an interferogram is measured.

20. The system as in claim 5 wherein at least one of said measurement heads is configured to make spectral measurements in the infrared spectral range.

21. The system as in claim 5 wherein at least one of said measurement heads is configured to make spectral measurements in the visible spectral range.

22. The system as in claim 5 wherein at least one of said measurement heads is configured to make spectral measurements in the ultra-violet spectral range.

23. The system as in claim 5 wherein at least one of said measurement heads is configured to make spectral measurements in the x-ray spectral range.

24. The system as in claim 5 wherein optical components of at least one of said measurement heads is suspended on a flexible mount.

25. The system as in claim 1 wherein said system is configured to have power tool like ergonomics.

26. The system as in claim 1 wherein said at least one detachable measurement head is a gas cell measuring head.

27. The system as in claim 1 wherein said at least one detachable measurement head is a surface reflectance measuring head.

28. The system as in claim 1 wherein said at least one detachable measurement head is a a surface reflectance measuring head that includes and integrating sphere.

29. The system as in claim 1 wherein said at least one detachable measurement head is a specular reflectance measuring head.

30. The system as in claim 1 wherein said at least one detachable measurement head is a grazing angle measuring head.

31. The system as in claim 1 wherein said at least one detachable measurement head is an attenuated total reflectance measuring head.

32. The system as in claim 1 wherein said at least one detachable measurement head is a diffuse reflection measuring head.

33. The system as in claim 1 wherein said at least one detachable measurement head is a non-volatile residues measuring head.

34. The system as in claim 1 wherein said at least one detachable measurement head is a directional hemisphere reflectance measuring head.

35. The system as in claim 1 wherein said at least one detachable measurement head is a liquid transmission cell measuring head.

36. The system as in claim 1 wherein said at least one detachable measurement head is a fluorescence measuring head.

37. The system as in claim 1 wherein said spectrometer is a filter-based spectrometer.

38. The system as in claim 1 wherein said spectrometer is a prisms-based spectrometer.

39. The system as in claim 1 wherein said spectrometer is a gratings-based spectrometer.

40. The system as in claim 1 wherein said spectrometer is an interferometer-based spectrometer.

41. The system as in claim 1 wherein said spectrometer is a filter-based spectrometer.

* * * * *